United States Patent
Peschechera et al.

(10) Patent No.: US 11,684,623 B2
(45) Date of Patent: Jun. 27, 2023

(54) SOLUBLE MELATONIN TRIPARTATE ADDUCT FOR THE PREVENTION AND TREATMENT OF RARE AND SEVERE EYE SIGHT-THREATENING CONDITIONS AND NEURO-OPHTHALMIC DISORDERS

(71) Applicant: WORPHMED SRL, Milan (IT)

(72) Inventors: Emanuela Peschechera, Milan (IT); Paolo Alberto Veronesi, Milan (IT)

(73) Assignee: WORPHMED SRL, Milan (IT)

( * ) Notice: Subject to any disclaimer, the term of this patent is extended or adjusted under 35 U.S.C. 154(b) by 0 days.

(21) Appl. No.: 17/790,808

(22) PCT Filed: Dec. 17, 2020

(86) PCT No.: PCT/EP2020/025589
§ 371 (c)(1),
(2) Date: Jul. 5, 2022

(87) PCT Pub. No.: WO2021/139872
PCT Pub. Date: Jul. 15, 2021

(65) Prior Publication Data
US 2023/0061569 A1    Mar. 2, 2023

(30) Foreign Application Priority Data
Jan. 8, 2020    (IT) .................. 102020000000139

(51) Int. Cl.
*A61K 31/52* (2006.01)
*A61P 27/02* (2006.01)
*A61K 9/00* (2006.01)
*A61K 9/06* (2006.01)
*A61K 9/19* (2006.01)
*A61K 47/18* (2017.01)
*A61K 47/26* (2006.01)

(52) U.S. Cl.
CPC ............ *A61K 31/52* (2013.01); *A61K 9/0048* (2013.01); *A61K 9/06* (2013.01); *A61K 9/19* (2013.01); *A61K 47/183* (2013.01); *A61K 47/26* (2013.01); *A61P 27/02* (2018.01)

(58) Field of Classification Search
CPC ........ A61K 31/52; A61K 9/0048; A61K 9/06; A61K 9/19; A61K 47/183; A61K 47/26; A61P 27/02
See application file for complete search history.

(56) References Cited

PUBLICATIONS

Andrew W. Siu et al., "Protective effects of melatonin in experimental free radical-related ocular diseases", Journal of Pineal Research, vol. 40, No. 2, Mar. 1, 2016, pp. 101-109.
Handbook of Pharmaceutical Excipients, 7th Edition, 2013, pp. 268-270, London—Philadelphia.
Handbook of Pharmaceutical Excipients, 7th Edition, pp. 219-221, paragraph 14 "Safety", London—Philadelphia.

*Primary Examiner* — Genevieve S Alley
(74) *Attorney, Agent, or Firm* — Standley Law Group LLP; Adam Smith

(57) ABSTRACT

The invention relates to soluble melatonin tripartate adduct comprising three structurally distinct regions and optionally trehalose, its stable sterile lyophilized powder and preservative-free aqueous solution or ointment, and to related pharmaceutical forms thereof, wherein the active melatonin moiety is adducted to a nucleoside in an optimal ratio range, with or without the presence of $C_2$-$C_5$ short chain amino acid. The invention further relates to the pharmaceutical field, more precisely it refers to the ophthalmic use of said melatonin tripartate adduct and to the method to prevent or treat serious ophthalmic pathologies in mammals and humans, more precisely rare and severe eye sight-threatening conditions and neuro-ophthalmic disorders in human and veterinary medicine, wherein said acute and chronic pathophysiological alterations and oculopathies are mainly caused by oxidative stress and related hypoxia-inducible factors (HIFs) and inflammation affecting the eyes. The pharmaceutical composition of said melatonin tripartate adduct may optionally contain either retinol or sodium hyaluronidate, or hyaluronic acid, L-carnosine, L-acetylcarnosine or a mixture thereof. Viscosity enhancers may be optionally included in the composition. Furthermore, the pharmaceutical composition of the invention is chemically and physically stable and safe.

22 Claims, No Drawings

SOLUBLE MELATONIN TRIPARTATE ADDUCT FOR THE PREVENTION AND TREATMENT OF RARE AND SEVERE EYE SIGHT-THREATENING CONDITIONS AND NEURO-OPHTHALMIC DISORDERS

TECHNICAL FIELD

The invention relates to the pharmaceutical field, more precisely it refers to the prevention and treatment of rare and severe eye sight-threatening oculopathies in human and veterinary medicine. More precisely the present invention relates to soluble melatonin tripartate adduct comprising three structurally distinct regions and optionally trehalose. The present invention further relates to a preservative-free pharmaceutical composition consisting of sterile lyophilised powder of melatonin tripartate (MTA) or of its sterile aqueous solution or ointment and to related pharmaceutical forms thereof, wherein the active moiety melatonin is adducted to a nucleoside in an optimal ratio range, with or without the presence of a $C_2$-$C_5$ low-chain amino acid. The pharmaceutical solution or the ointment or any other pharmaceutical composition thereof related to the present intention is characterized to contain said melatonin tripartate adduct at a concentration such as to produce the desired pharmacological effects of preventive and therapeutic nature on rare and severe eye sight-threatening ocular diseases and neuro-ophthalmic disorders. Hence the preservative-free composition of the invention suitably provides the therapeutically effective amount of the pharmaceutical product for the purpose for which it has been conceived and designed. In another further embodiment said pharmaceutical composition may also optionally contain retinol or sodium yaluronate, yaluronic acid, L-carnosine, L-acetylcarnosine or a mixture thereof.

The distinctive characteristic of the invention further relates to the use of said pharmaceutical composition characterized that an effective amount of melatonin tripartate adduct (lyophilized sterile stable powder) conveniently admixed to trehalose and dissolved in sterile water or saline solution or admixed to any other suitable pharmaceutical carriers shows a much better diffusion in the biological liquids, cells, tissues and organs, and therefore a better bioavailability rather than melatonin, a lipophile molecule that is notoriously practically insoluble in water.

Tripartate melatonin adduct and its sterile preservative-free aqueous solution is particularly suitable for preventing or treating acute and chronic pathological changes and diseases caused by excessive oxidative stress, overexpressed from by hypoxia inducible factors (HIFs) or inflammation particularly affecting the eyes.

The invention is further characterized by the technological peculiarity that the tripartate melatonin adduct is surprisingly converted from a lipophilic active substance practically insoluble in water into a water-soluble adduct, more diffusible which therefore penetrates better into cells, tissues and organs, thus promptly and significantly decreasing the oxidative stress caused by HIFs, inflammation and related alterations, with a remarkable decrease in the apoptotic process, repair of biological damage and tissue or organ lesions, thus restoring eye homeostasis. A particular embodiment of the present invention is consisting in the fact that the new pharmaceutical composition is suitable for treating severe acute, chronic and degenerative oculopathies affecting both mammals and humans. The beneficial effects of said ophthalmic composition are more evident when melatonin tripartate is used to prevent and/or treat the damages from periocular oxidative stress and inflammatory processes and when the therapeutically effective amount of said pharmaceutical composition for ophthalmic use, free of preservatives, is dispensed by means of sterile single-dose containers or preferably in a new multidose bottle, which provides for each delivery an exact metered volume of a single eye drop, to prevent or treat eye diseases and other eye conditions that require a necessary exogenous supply of melatonin, such as pathological conditions that expose patients to the risk of blindness, such as retinopathy of prematurity (ROP), uveitis, glaucoma (ocular hypertension) cataract, cataracts in babies, strabismus, age-related macular degeneration (AMD), diabetic macular degeneration (DMD), diabetic macular edema (DME), proliferative diabetic retinopathy, retinitis pigmentosa (RP), pathological myopia (PM), photocheratitis, amblyopia, chorioretinopathy, diabetic retinopathy, retinal glaucomatous, diabetic acute and chronic damages, retinal detachment, tears dry eye syndrome (DES), choroidal neovascularisation (CNV), retinal vein occlusion (RVE) retinitis, optic neuritis (ON), and other eye dysfunctions often occurring in the event of scarce endocrine production of melatonin or in presence of an excessive acute or chronic oxidative stress condition as eye strain and other common symptoms of computer vision syndrome or display device syndrome (CVS), ocular changes after space travel, eye infectious diseases such as trachoma caused by *Chlamydia trachomatis*, ocular toxoplasmosis and malaria uveitis, Ebola virus disease-related uveitis in survivors during convalescence, or other emerging causes of viral-associated posterior uveitis infections, a significant cause of sight-threatening ocular diseases in the posterior segment, that include human herpes viruses, measles, rubella, and arboviruses such as Dengue, West Nile, Chikungunya, Coronavirus (SARS-CoV2) and Zika, a spectrum of inflammatory eye disease leading to eye pain, redness, and vision loss or when an additional support of exogenous melatonin is required as during and post-ophthalmic interventions or surgery-induced inflammation and oxidative stress with the aim to reduce and control the overexpressed stress condition.

More particularly, the effects of the pharmaceutical composition of the invention are very advantageous for preventing and treating retinopathy of prematurity in premature and full-term infants, as it has been shown that melatonin systemically prevents pathological neovascularisation, protects the cells of the glia and elicits anti-inflammatory effects through inhibition of the HIF-1α/VEGF (vascular endothelial growth factor) biological pathway in oxygen-induced retinopathy. This experimental experience in laboratory animals was conducted by dissolving melatonin in organic solvents, unsuitable for human use, and only using the systemic route (oral, intraperintoneal or injectable administration).

In a further preferred embodiment a sterile preservative-free suitable solution of melatonin tripartate is obtained, by dissolving the sterile lyophilized mixture of melatonin tripartate adduct and trehalose in water or in saline solution to avoid the use of organic solvents similar to dimethyl sulfoxide (DMSO), which, however, laboratory experiments on animals have shown is able to induce the release of histamine and that after prolonged use cause changes in the cornea, so that consequently its use it cannot be certainly recommended in neonatology, medicine and patients suffering from certain pathologies.

Furthermore, more particularly in relation to the specific ophthalmic use, a skilled expert in the art shall further know that DMSO can further increase the intraocular pressure and consequently is contraindicated in those eye pathologies characterized by high ocular pressure, like glaucoma as reported in specialized publications (Handbook of Pharmaceutical Excipients, 7th Edition, 2013, page 268-70). As a consequence, DMSO is namely contraindicated as vehicle or carrier for many other preparations intended for ophthalmic use, and not only.

Definitions

As referred herein, the term "activated melatonin" it is understood to mean the moiety of the adduct tripartate where certain parts of the molecule melatonin are partially activated/polarized thus showing a biologically increased reactivity.

As used herein, the term "eye diseases" it is understood to mean oculopathies, eye disorders and related symptoms including, but not limited to, cataract, open-angle primary glaucoma (POAG), corneal disorders, presbyopia, computer vision syndrome or display device syndrome (CVS), eye strain, ocular inflammation, blurred vision, dry eye syndrome (DES), retinal diseases, vitreous opacities and lesions, complications of diabetes mellitus, and macular and other retinal diseases.

As used herein, the term "ophthalmic composition" refers to a pharmaceutical mixture suitable for administration into the eye or ocular surface. Ocular compositions include preparations, solutions, gels, ointments, emulsions, strips, and the like.

As used herein the term "sterile preparation" includes any preservative-free sterile ophthalmic pharmaceutical composition for direct administration to any part of a mammalian eyes, including implantation, injection, administration as a drop, gel or wash, and the like, wherein the preparation is substantially free from undesired foreign matter just prior to dispensing administration. Methods for ensuring sterility include aseptic packaging of a sterile product and sterilization by sterilizing filtration, exposure to radiation, heat combinations thereof and the like.

As referred in the present invention, the term "safe" means a chemical adduct and a pharmaceutical formulation thereof satisfying the well known criteria for medicinal products, a s well tolerated by neonates, newborn, pediatric or adult patients and devoid of any excipients not pharmaceutically acceptable, harmful, antigenic or toxic.

As referred in the present invention, the term "chemically stable" refers to a formulation that, upon storage at room temperature (25° C.±2° C.) for at least one day or more months, as it will be established from appropriate stability studies, or preferably one week or even up to 3 months, as generally prescribed for galenical preparations, or more in case of industrial preparations should not show drug loss of the powder adduct in the pharmaceutical solution, without melatonin degradation.

As referred in the present invention, for a composition, the expression "physically stable" refers to a formulation that, at room temperature (25° C.±2° C.), exhibits substantially no growth in particle size during storage for at least three days, preferably one week, that remains transparent or readily redispersible, and upon redispersion, neither agglomerates nor quick separates from the aqueous vehicle so to maintain uniform distribution of the active ingredient and of its dosing aliquots.

As referred in the present invention, by "physiological saline solution" or "saline solution" is meant a sodium chloride solution in purified water or, preferably, in water for injectable preparations (in the following abbreviated by "water for injections"). The water distilled under these conditions is sterile and apyrogen.

The term "prophylaxis" and/or "prevention" or "preventing" refers to the therapeutic use of the adduct for reducing the occurrence of a disease, while the term "treatment" refers to the therapeutic use of the adduct of the invention for palliative, curing, symptom-alleviating, symptom-reducing, disease regression-inducing therapy.

As used herein the terms "therapeutically effective amount" or "effective dose" and "effective regimen" whenever applied to melatonin tripartate means the adequate amount of pharmaceutical composition of the invention to conveniently elicit or to maintain the desired pharmacological or therapeutic effects and that when the medicinal adduct is administered to patients, delivers a quantity of melatonin, suitable to provide the desired biological and clinical outcome.

As used herein, the term "individual" or "subject" includes humans and vertebrates.

As used herein the term "ocular surface" includes the wet-surfaced and glandular epithelia of the cornea, conjunctiva, lacrimal gland, accessory lacrimal glands, nasolacrimal duct and Meibomian gland, and their apical and basal matrices, puncta and adjacent or related structures, including the eyelids linked as a functional system by both continuity of epithelia, by innervation, and the endocrine and immune systems.

As used herein the term "intraocular" includes the application onto the posterior segment of the eye of the cornea, into the invitreal cavity, conjunctiva, lacrimal gland, accessory lacrimal glands, nasolacrimal duct and Meibomian gland, and their apical and basal matrices, puncta and adjacent or related structures, including the eyelids linked as a functional system by both continuity of epithelia, by innervation, and the endocrine and immune systems.

As used herein the term "ophthalmic viscosurgical devices (OVDs)" are a class of gel-like, clear solutions or substances with different quality characteristics that are used in refractive and intraocular surgery for safer maneuvers in the anterior and posterior chamber. OVDs differ in the rheologic polymer type(s), concentration, and chain length. Their major role is to create and maintain volume in the anterior chamber of the eye and protect the corneal endothelium during particular steps of the ophthalmic procedure. They are commonly based on HPMC (hydroxypropylmethylcellulose) or CMC (carboxymethylcellulose) or sodium hyaluronate, and their different qualities determine their physical and chemical condition, e.g. viscosity, elasticity, and cohesion.

STATE OF THE ART

A significant number of severe and rare eye conditions and of other long-term debilitating and sight-threatening ocular diseases are associates to oxidative stress, inflammation and irritation caused from free radicals (ROS) and involving overexpressed vascularisation of HIF-1α/VEGF pathway. Free radicals are molecular species having a single unpaired electron available in an outer orbital. Free radicals can initiate chain reactions in cells and body fluids that damage organic molecules, including biomolecules (e.g., DNA, lipids, and proteins). Free radicals are formed endogenously (e.g., by cellular metabolism, inflammation by immune cells, and the like) and exogenously (e.g., by radiation, pharmaceuticals, hydrogen peroxide, toxic chemicals, smoke, alcohol, oxidized polyunsaturated fats, and the like). More particularly, eyes are exposed to light whenever are open or not, and light entering the eye may generate superoxide radicals. Once generated, the superoxide radical may degenerate into other free radicals such as hydrogen peroxide and hydroxide radicals.

Oxidative stress (OS) is associated to a pleiotropic variety of ocular disorders and to retinal misalignments and eye diseases such as cataracts (a loss of transparency of the lens, in view that free radicals may oxidize the proteins of the lens, which may damage the protein structure of the lens.), glaucoma, diabetic retinopathy, and macular degeneration. More particularly, OS has been reported by ophthalmologists as the main cause of a variety of ocular disorders and pathological conditions in patients at risk of blindness, such as retinopathy of prematurity (ROP), uveitis, glaucoma (ocular hypertension) cataract, cataracts in babies, strabismus, age-related macular degeneration (AMD), diabetic macular degeneration (DMD), diabetic macular edema (DME), proliferative diabetic retinopathy, retinitis pigmentosa (RP), pathological myopia (PM), photocheratitis, amblyopia, chorioretinopathy, choroideremia, retinal glaucomatous, diabetic acute and chronic damages, retinal detachment, tears dry eye syndrome (DES), choroidal neovascularization (CNV), retinal vein occlusion (RVE) retinitis, optic neuritis (ON), and other eye dysfunctions often occurring in the event of scarce endocrine production of melatonin or in presence of an excessive acute or chronic oxidative stress condition as eye strain and other common symptoms of computer vision syndrome or display device syndrome (CVS), ocular changes after space travel, eye infectious diseases such as trachoma caused by *Chlamydia trachomatis*, ocular toxoplasmosis and malaria uveitis, Ebola virus disease-related uveitis in survivors during convalescence, or other emerging causes of viral-associated posterior uveitis infections, are a significant cause of sight-threatening ocular diseases in the posterior segment, that include human herpes viruses, measles, rubella, and arboviruses such as Dengue, West Nile, Chikungunya, Zika virus, and Coronavirus (SARS-CoV2) a large spectrum of inflammatory eye disease that, if untreated, might progressively lead to worsening conditions and to blindness.

Similarly, a large spectrum of other inflammatory eye conditions leading to eye pain, redness, and vision loss would often require an additional support of exogenous melatonin as well during and post-ophthalmic interventions or surgery-induced inflammation and oxidative stress, with the aim to reduce and control the overexpressed stress condition.

It is already known that certain antioxidants molecules are capable of scavenging free radicals and subsequently protecting cells from damage due to oxidative stress. Antioxidants protect cells from free radicals by inhibiting free radical formation, intercepting free radicals, and repairing free-radical-induced injury. However, a suitable application and delivery method of an antioxidant into any parts of the eye seems to result complex and rather difficult.

In fact, topical administration is the most common and convenient route for ocular drug delivery. Consequently, the cornea, conjunctiva, and sclera form the most essential barriers for drug penetration into the intraocular tissues. The cornea is an important mechanical barrier protecting the intraocular tissues. It is considered to be the main pathway for ocular penetration of topically applied drugs. Since the cornea exhibits hydrophilic as well as lipophilic characteristics, it represents an effective barrier for diffusion of both hydrophilic and lipophilic substances. Consequently, corneal absorption is considered to be the major penetration pathway for topically applied drugs, but a technical challenge as well.

Now applicant considers that it is urgent to explore and develop pharmaceutical compositions in the ophthalmological field to provide active antioxidants in sufficient amounts to be delivered locally directly into an eye thus avoiding the systemic administration route, but without the risk for common adverse reactions due to the application, such as reported ocular adverse reactions as eye pain, ocular hyperaemia, increased intraocular pressure, vitritis, vitreous detachment, retinal haemorrhage, visual disturbance, vitreous floaters, conjunctival haemorrhage, eye irritation, foreign body sensation in eyes, increased lacrimation, blepharitis, dry eye and eye pruritus and the like. However, until now the ophthalmic pathologies have been mainly treated by eliminating the symptoms. For instance, pharmacological treatments for ocular diseases as glaucoma have been focused to reduce the intraocular pressure (IOP) by administering a betablocker either systemically or locally with eye drops while for others as uveitis, retinitis and dry eye syndrome palliative treatments are currently used aiming to reduce or minimise those pathological effects. More precisely, for uveitis first treatment options are corticosteroids, used to reduce the inflammation by lowering the activity of the immune system or immunosuppressant agents such as cyclosporin. For retinopathy of prematurity, the attempts done with an ophthalmic solution of the betabloker propranolol 0.1% were not successful. No better results were recently achieved even with 0.2% solution of the same betablocker. More recently hyaluronic acid has been also introduced as eye drop lubricant for the palliative treatment of some other conditions, but without significant advantages, while many other oculopathies still remain unmet clinical needs. The main ophthalmic pathologies for which until now satisfactory therapies have not yet been reported are:

Retinopathy of prematurity (ROP)—Preferably preterm—but also, in certain stressing conditions, at term-infants are at birth either naturally exposed to hyperoxic challenge due to the transition from the hypoxic intrauterine environment to extrauterine life, and this gap is even more significant for neonates that require supplemental oxygen during resuscitation in the delivery room, or more susceptible to infection, especially if born prematurely, or with reduced antioxidant defences. Retinopathy of prematurity, identified by neonatologists/ophthalmologists with the acronym "ROP", affects particularly premature newborns (early gestational age <31 weeks gestation and/or low birth weight <1250 grams). A severe ROP condition can cause the retina to pull away or detach from the wall of the eye, so even cause blindness. Improved survival of premature infants led to more infants being at risk of developing ROP, that therefore remains the main cause of childhood blindness. ROP accounts for up to 60% of pediatric blindness and incidence is ranging from 9 to 60 per 1,000 life-births in some developing countries. This increased incidence of ROP due that more immature infants are surviving has been referred to as the "third epidemic of ROP" so that an accurate screening is strongly recommended by World Health Organization (WHO/OMS) and by national and international Associations of Neonatology and Ophthalmology.

Moreover, since decades scientists and ophthalmologists made several different attempts to counteract other eye pathologies consequent to the damaging effects of free-radicals into retina, satellite tissues and connected organs or parts thereof, but up to date no satisfactory medicinal products have been developed for the prevention and/or treatment of said serious conditions and diseases as:

Central serious chorioretinopathy (CSCR) is a relatively common cause of visual impairment in the Western world, and is characterized by the accumulation of subretinal fluid in the macula. The disease classically affects men between the ages of 20 and 50 and has been associated with corticosteroid exposure, phosphodiesterase inhibitor use and obstructive sleep apnea. Patients can present with a variety of visual symptoms including relative central scotoma, metamorphopsia, dyschromatopsia and micropsia. On examination, the characteristic finding is a posterior neurosensory retinal detachment caused by leakage of fluid from the level of the retinal pigment epithelium. There is no gold standard for treatment options of persistent CSCR, and a number of therapies have been tried with varying success. Focal laser photocoagulation to pinpoint areas of leakage on fluorescein angiography (FA) was the first treatment shown to be of some benefit for CSCR. However, photocoagulation is destructive, can lead to symptomatic scotomas, and occasionally formation of secondary choroidal neovascularisation. CSCR can also lead to permanent vision loss.

Uveitis occurs when the middle layer of the eyeball gets inflamed (red and swollen). This layer, called the uvea, has many blood vessels that nourish the eye, and uveitis can damage vital eye tissue, leading to permanent vision loss. There are 3 types of uveitis, and they are based on which part of the uvea is affected. Symptoms can include having a red eye, with or without pain, or being very sensitive to bright light or having blurry vision or seeing "floaters" (specks or moving clouds in the vision) all of a sudden.

Emerging viral-associated posterior uveitis infections are a significant cause of sight-threatening ocular diseases in the posterior segment, as Ebola virus disease-related uveitis in survivors during convalescence, condition that further include human herpes viruses, measles, rubella, and arboviruses such as Dengue, West Nile, Chikungunya, Zika and Coronavirus, in other words a spectrum of inflammatory viral-related eye diseases leading to eye pain, redness, and vision loss, all still remain without an appropriate pharmacological intervention.

It has already been reported previously that Coronavirus can be associated with conjunctivitis in humans. Additionally, other retinal disorders, such as retinal vasculitis, retinal degeneration, and blood-retinal barrier tears have been observed in experimental animal models of the coronavirus. Furthermore, infectious ophthalmic complications from SARS-CoV-2 have not been described frequently (it seems to affect around 3-4% of patients). In addition, viral loads in ocular tissues have yet to be the subject of more careful studies.

Trachoma is an infectious disease caused by bacterium *Chlamydia trachomatis*. The infection causes a roughening of the inner surface of the eyelids. This roughening can lead to pain in the eyes, breakdown of the outer surface or cornea of the eyes, and eventual blindness. Untreated, repeated trachoma infections can result in a form of permanent blindness. Children spread the disease more often than adults.

Syphilitic chorioretinitis should be included in differential diagnosis of any form of ocular inflammation. There is a significantly higher proportion of human immunodeficiency virus (HIV)-positive patients with ocular syphilis compared to HIV-negative cases. However, the clinical signs and symptoms are more insidious in HIV-negative patients who are easily misdiagnosed. The common manifestations of syphilitic chorioretinitis were uveitis, retinal vasculitis, and optic neuritis.

Retinitis pigmentosa (RP) comprises a group of incurable inherited retinal degenerations. Targeting common processes, instead of mutation-specific treatment, has proven to be an innovative strategy to combat debilitating retinal degeneration. Growing evidence indicates that deficiency of melatonin could be responsible of related neurodegenerative disorders, including apoptosis and inflammation.

Diabetic retinopathy (DR) is a frequent microvascular problem associated with diabetes mellitus, is the main cause of blindness worldwide. Timely interferences for those at high risk of sight-threatening problems linked to DR include diabetic macular edema and proliferative DR (PDR), is critical to preventing vision loss; however, the molecular mechanisms underlying DR pathogenesis are poorly understood. Innate immunity and the dysregulation of inflammatory processes are currently thought to be important in the induction and advancement of DR, but the mechanism by which chronic hyperglycemia induces an immune response and DR still remains unclear.

Glaucoma is a leading cause of irreversible blindness worldwide, and provokes progressive visual impairment attributable to the dysfunction and loss of retinal ganglion cells and optic nerve axons. Glaucoma is almost characterized by an elevated intraocular pressure which produces pathological changes in the optical disc, with consequent appearance of various vision defects. Currently, clinical interventions for glaucoma are mainly restricted to the reduction of intraocular pressure, one of the major risk factors for the disease. One of the most used medicinal product for glaucoma contains timolol, a non-selective β-adrenergic blocker, available at 0.1% as ophthalmic gel and 0.5% eye drops. Nevertheless, timolol presents incompatibilities with benzalkonium chloride, the most used preserving agent for collyria, and interactions with many other medicinal products and other forms of interaction have been reported. However, lowering intraocular pressure is often insufficient to halt or reverse the progress of visual loss, underlining the need for the development of alternative treatment strategies. Recently, some clinicians reviewed the strategies to reduce oxidative stress in glaucoma patients. In fact, primary glaucoma is a multifactorial pathology involving a variety of pathogenic mechanisms, mainly including oxidative/nitrosative stress (OS/ON). Other studies suggested that antioxidants, among them vitamins B3, C and E, coenzyme Q10 and other natural compounds (such as coffee, green tea, gingko *biloba, coleus*, tropical fruits, etc.)

may help to regulate the intraocular pressure as well as protect the retinal neurons against oxidative/nitrosative stress (O&NS) in glaucoma.

Optic neuritis (ON) is the most common optic neuropathy affecting young adults, is a condition involving primary inflammation, demyelination, and axonal injury in the optic nerve which leads to retinal ganglion cell death and visual dysfunction. Although corticosteroids are the current mainstays of therapy for the treatment of optic neuritis, they fail to achieve long-term benefit on functional recovery, and provoke considerable side effects.

It is well known in the art that melatonin plays a central role in wide physiological functions and in the regulation of visual and neuroimmunological functions in the prematurity but also in aging and degenerative oculopathies as well.

However, it is also known that melatonin regulates the levels of oxidative markers, endogenous antioxidant status, and proinflammatory cytokines. In humans, melatonin (N-acetyl-5-methoxytryptamine) is an endogenous neurohormone secreted primarily from the pineal gland and to a lesser extent by extra pineal tissues such as the retina, harderian gland, and gastrointestinal tract Various studies in literature have shown that melatonin is able to have therapeutic functions in human disorders, caused by inflammation and oxidative stress, like rare and serious ocular pathologies. Some authors have recently evaluated in non clinical studies the effect of melatonin on the blood-retinal barrier and oxidative status of the vitreous in rats with oxygen-induced retinopathy (OIR), which is the commonly accepted animal model in the investigation of the ROP and other ischemic retinopathies. In said nonclinical studies melatonin has been administered by oral route (with the disadvantage of a scarce absorption rate of about 4%) or by systemic route, generally dissolved in an organic solvent as dimethyl sulfoxide (DMSO) neither suitable for humans not compatible with the eyes.

A skilled person would immediately arrive that an ambitious target would be the translation of those favourable preclinical results into the human clinical practice and that the real challenge would be the development of a novel pharmaceutical composition of melatonin designed and suitable for ophthalmic use, since until now a stable preservative-free sterile pharmaceutical solution of melatonin (more soluble and diffusible), the most appropriate pharmaceutical form for prevention and treatment of ocular diseases is not yet available on the market.

In fact, some formulations of melatonin disclosed in literature are either inadequate or unsatisfactory for said eye pathological conditions, mainly due for their scarce compliance due the presence of organic solvents, as DMSO and the like, or have been erroneously declared "soluble" but their water solubility and pH, stability or low concentrations are either inappropriate, insufficient or unsatisfactory for their intended ophthalmic use, effective dose and effective regimen.

More particularly it is well known to the experts of the art that DMSO (dimethyl sulfoxide) has precautionary information as induced release of histamine, long term produces ocular lens changes, administered intravenously will cause significant haemolysis, and has been associated with hemoglobinemia, acute colic, diarrhea, myositis, muscle tremors, and collapse, and as strong solvent it may act as a penetration enhancers and increase transmembrane penetration of other compounds. In view of this unsatisfactory background, further investigations and efforts have been done by the applicant to obtain a pharmaceutical formulation of melatonin solution, characterized by a satisfactory stability, solubility and biocompatibility, having as main feature to be administered to mammals and humans (premature babies, newborns, toddlers or adults) by intraocular and on eye surface routes, that shall further exclude the use of organic solvents and of preserving agents, in order to avoid adverse effects and/or incompatibilities with said tissues and organs, while showing a physiological pH range of 7.2±0.2, more preferably about 7.4, and a suitable osmolarity interval as well.

The instant invention surprisingly resolve those major problems providing a lyophilized powder of melatonin tripartate adduct and trehalose and its pharmaceutical aqueous sterile preservative-free solution as well that would be advantageously administered by local route as aqueous solution, preferably as collyria or instillations or eye drops to prevent or treat most pathological eye diseases caused by oxidative stress and/or inflammation particularly in the ophthalmic field in premature babies, newborns, infants, toddlers and adults.

The melatonin tripartate adduct may also be advantageously used for the preparation of a sterile ophthalmic ointment compounding it with one or more suitable excipients in order to achieve a long lasting effect after application on the ocular surface.

SUMMARY OF THE INVENTION

This invention relates to soluble melatonin tripartate adduct comprising three structurally distinct regions and optionally trehalose and to the stable sterile lyophilized powder, aqueous solution or ointment and other related pharmaceutical forms thereof, wherein melatonin is combined with a nucleoside in an optimal ratio range, with or without the presence of $C_2$-$C_5$ low-chain amino acid.

The invention further relates to a sterile pharmaceutically acceptable composition containing said melatonin tripartate adduct, and to its use to prevent and treat some oculopathies in mammals and humans (prematures, newborns, infants, young people, toddlers and adults).

Now, the applicant has surprisingly found that a soluble powder mixture of melatonin tripartate adduct of the invention and of the disaccharide trehalose, suitably dissolved in a sterile preservative-free aqueous solution thereof, can be advantageously used to treat severe eye diseases in humans, particularly when the acute and chronic physiopathological alterations and misalignments are caused by oxidative stress and by inflammation involving the eyes as retinopathy of prematurity (ROP) and other neonatal ophthalmic injuries.

The feature of the invention is further addressed to yield a suitable pharmaceutical composition targeting other specific organs and/or indications.

In relation to the other regions of melatonin tripartate adduct there is no much to say rather than at certain ratio they advantageously function as efficient complexing agents and stabilizers. In particular, the nucleoside moiety adenosine is an important component incorporated in the adduct and an attractive target for therapeutic approaches, more particularly when the adduct of the invention is intended to prevent or treat ocular inflammatory diseases, considering its additional neuroprotective properties already confirmed in animal experiments.

However, $C_2$-$C_5$ low-chain amino acid glycine is the other important component incorporated in the adduct further useful to achieve a satisfactory lyophilisation process while trehalose (two glucose units linked together in a α-1,1-glycosidic linkage. i.e., α-d-glucopyranosyl α-d-glucopyranoside) is a complexing agent, humectant, viscosity increasing agent, lyophilisation aid, that contributes to the stabilisation during the freeze-thaw and lyophilisation of the adduct. A particular embodiment of the instant invention is that said adduct is a chemically and physically stable powder or aqueous solution or ophthalmic ointment thereof at the most appropriate concentration to be advantageously administered as pharmaceutical formulations suitable for ocular administration, thus providing the most convenient bioavailability rather melatonin alone, in order to achieve the desired and effective medical treatment.

Another surprising embodiment of the pharmaceutical composition comprising melatonin tripartate adduct is that advantageously avoids the use of DMSO, being the adduct soluble in water. In fact, it is well known to the experts in the art that dimethyl sulfoxide can increase the intraocular pressure (see Handbook of Pharmaceutical Excipients, 7th Ed, pages 219-221, paragraph 14 "Safety") and consequently it is not recommended in pathological ophthalmic conditions characterized by ocular high pressure, like glaucoma.

Furthermore, in another preferred embodiment the pharmaceutical composition of the invention comprises melatonin tripartate adduct either admixed to HPMC (hydroxypropylmethylcellulose) or CMC (carboxymethylcellulose) or sodium hyaluronate or hyaluronic acid, generally in the range of about 1-2%, to yield an ophthalmic solution or device with a viscosity suitable for ophthalmic surgery (ophthalmic viscosurgical devices, OVDs), glaucoma, strabismus and cataract, compatible with human aqueous humour, with regard to osmolarity, ionic strength and pH 7.2±0.2, ideally at pH about 7.4. A major aim of the invention is further to yield an ophthalmic aqueous solution of melatonin tripartate adduct particularly convenient to prevent or treat serious neonatal eye diseases, such as retinopathy of prematurity (ROP), and other serious ocular diseases, as strabismus, cataract, glaucoma, and retinal inflammatory conditions, as uveitis, degenerative, diabetic retinopathy, in paediatric and adult patients or even in the veterinary field. A more specific embodiment of the composition of the invention is that the ophthalmic solution thereof is dispensed as sterile monodose strips for eye drops containing a volume from 0.1 ml to 0.5 ml or more preferably by a multi dose-preservative-free delivery system, particularly advantageous for ocular delivery administration.

The compositions of the present invention may be further used to treat, among other things, irritation, dryness of the eye, and the onset or progression of an eye disease. The present invention provides medicinal compositions that may be further used to maintain eye health as well the as other eyesight and to prevent or treat eye diseases. Melatonin tripartate adduct is further compatible with any other ophthalmic preventive or systemic treatments containing active substances for associated pathologies.

Other features and advantages of the present invention will be readily apparent to those skilled in the art upon a reading of the description of the embodiments that follows.

DETAILED DISCLOSURE OF THE INVENTION

The present specification is providing melatonin tripartate adduct comprising three structurally distinct regions and optionally trehalose and to its stable sterile lyophilized powder and aqueous solution or ointment and other related pharmaceutical forms thereof, wherein melatonin is activated and adducted to the nucleoside adenosine at the optimal molar ratio range, in presence of the low-chain amino acid glycine.

The specification further provides a sterile preservative-free pharmaceutical formulation, containing a lyophilized mixture of the novel adduct melatonin tripartate and the disaccharide trehalose dissolved in sterile water solution or saline, suitable for ophthalmic administration, as eyes drops, instillation solutions and ointment, and at a convenient concentration to produce the desired pharmacological and medicinal effects for preventing and treating the clinical eye diseases for which the adduct has been designed. More particularly, said pharmaceutically stable solution of the invention can be suitably administered either as drops or as anti-oxidant coadjuvant solution in eye surgery (ophthalmic viscosurgical devices, OVDs).

A more preferred embodiment of the instant invention is that the novel composition is suitable for the treatment of serious ophthalmic neonatal diseases, as retinopathy of prematurity (ROP), but also for other serious ocular diseases, as uveitis, strabismus, cataract, glaucoma, diabetic retinopathy in other age-groups of patients. Another preferred advantageous embodiment of the invention is that the ophthalmic composition of the instant invention elicits favourable immunological effect in situ directly in the affected parts of the eye.

Moreover, another considerable advantage of the ophthalmic composition of the invention is that the delivery of melatonin tripartate adduct of the instant invention is performed without the intraocular injections as required when some other used substances, alike bevacizumab or ranibizumab or aflibercept, nowadays practiced into the eyes of adult patients affected by retinal degeneration (as for instance age-related macular degeneration, AMD)

In another embodiment, the total cranium irradiation of 5 Gy in a single dose may also be the main cause of lens opacification that induce or enhance the cataract formation. Applicant has surprisingly found that adjuvant treatment of melatonin tripartate adduct could protects the eye lenses from radiation-induced cataract formation. Therefore, the novel pharmaceutical composition of melatonin tripartate adduct could further reduce the eye burden to those patients suffering from toxic therapeutic regimens such as radiotherapy and/or chemotherapy and might provide an alleviation of the eye oxidative stress symptoms due to radiation-induced cataract eye injury.

The depletion in animals of their natural stores of important intracellular antioxidant (melatonin) and the elevation of lenticular $Ca(2+)$ by UV irradiation, may be further the main cause of lens opacification. The application of medicinal eye drop solution of melatonin tripartate adduct after UV radiation is an effective melatonin tripartate treatment concurrent with UV irradiation.

In conclusion, applicant surprisingly found that melatonin tripartate may protect the eye lens from the damaging effects of UV exposure, and its effects protect lens from oxidative stress, elevating $Ca(2+)$ levels, which are considered an important causes of cataractogenesis.

The melatonin tripartate adduct of the instant invention is schematically outlined by the following formula (I):

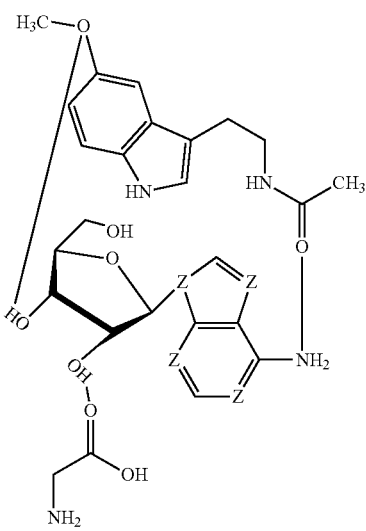

wherein melatonin is complexed with adenosine and glycine. Adenosine is a purine nucleoside consisting of adenine attached to a ribofuranose moiety via a β-$N_9$-glycosidic bond and the low-chain amino acid glycine is a $C_2$ amino acid having a single hydrogen atom as its side chain. Melatonin tripartate adduct is advantageously much more soluble in water than melatonin molecule, as reported in the following table:

| Solubility table in water (21.11° C.; 70° F. = room temperature) according to USP (*) and EP (#) | | |
|---|---|---|
| Active substance | Specifications (*)(#) (solute/solvent; w/v) | Results |
| melatonin | practically insoluble (v > than 10000) | 0.1 mg/1.0 ml |
| melatonin tripartate (1:4:1) | Soluble (v = 10-30) | 33.0 mg/1.0 ml | w = weight; v = volume
(*) USP = United States Pharmacopoeia (current edition)
(#) EP = European Pharmacopoeia (current edition)

The feature of the invention is further characterized to yield apharmaceutical composition by suitably dissolving or admixing said sterile powder mixture of melatonin tripartate adduct and pharmaceutical grade trehalose to yield an aqueous sterile preservative-free solution or the semisolid form of ointment. In another preferred embodiments said ophthalmic solution of the invention is comprising the steps of:

(i) preparing melatonin tripartate adduct (MTA) sterile lyophilized powder by adducting melatonin, adenosine and glycine at the optimal molar ratio of 1:4:1, by conventional lyophilisation process; and (ii) admixing in sterile environment said sterile lyophilized powder consisting of melatonin tripartate adduct in a desired volume of distilled water and then with an appropriate amount of pharmaceutical grade trehalose; and (iii) adding optionally retinol or sodium hyaluronate, hyaluronic acid, L-carnosine, L-acethylcarnosine each in a convenient amount or a mixture thereof, and admixing thoroughly to yield a clear and transparent solution; and (iv) adjusting the pH to about 7.4 and the osmolarity within the preferred parameters of 310 and 350 mOsm/kg; and (v) processing the bulk solution through a sterilizing membrane or cartridge filter of an appropriate efficiency to meet the sterility requirements; and (vi) apportioning a fixed volume of the preservative-free sterile ophthalmic solution into a primary monodose strip or multi-dose container equipped from a drop-metering device, using nitrogen as a purge and process gas. The preservative-free dispensing system is provided of a metering drop device allowing the application of said solution by ophthalmic route. Another main feature of the invention is that the sterile aqueous solution of the instant invention is obtained with the exclusion of organic solvents alike ethanol or dimethyl sulfoxide (DMSO) that in view of their precautionary information (adverse reactions, side effects, contraindications and precautions) are not recommended in patients affected by certain eye conditions and diseases, or even contraindicated ad in perineonatology and prematurity.

A particular embodiment of the instant invention is that the novel melatonin tripartate adduct is consisting by melatonin/nucleoside/low-chain amino acid in a molar ratio varying as from 1:1:1 up to of 1:6:1, more preferably 1:4:1. Another feature of the instant invention is that the pharmaceutically acceptable excipient trehalose is added at a suitable concentration that when dissolved is ranging a concentration from 1% to 5%, more preferably between 1.5 and 3%.

Another embodiment of the instant invention is that the powder mixture containing the melatonin adduct and trehalose is lyophilized by suitable methods well known to the experts of the arts. After lyophilisation, the sterile lyophilized powder is harvested and can be reconstituted before use in a suitable aqueous vehicle to provide the ready-to-use pharmaceutical formulation. In another embodiment the pharmaceutical formulation of the invention is sterile and sterilization can be achieved according to known methods. However, the dosage of the pharmaceutical composition of the instant invention containing melatonin tripartate adduct is expressed as concentration of melatonin, and shall be comprised between 0.01 mg/ml and 10 mg/ml, preferably between 0.05 mg/ml and 2.5 mg/ml in sterile distilled water or saline solution. A particular embodiment of the instant invention is that, when the solution is intended for ophthalmic use, the preferred molar ratio is 1:4:1 and the concentration of melatonin in the adduct is more advantageously of 0.5 mg/ml of distilled water or saline.

Another embodiment of the instant invention is that the pH range of the ocular formulation of the instant invention should have a pH range between 7.0 and 7.7, more preferably 7.2±0.2, optimally abut pH 7.4 to be compatible with the tears pH. When necessary pH adjustments can be achieved by using diluted hydrochloric acid (HCl) and sodium hydroxide (NaOH).

It is well known in the art that the osmolarity of the lacrimal fluid is mainly dependent on the number of ions dissolved in the aqueous layer of the tear film and normally ranges between 310 and 350 mOsm/kg. Moreover, hypotonic solutions are better tolerated by the ocular tissues than hypertonic ones, which lead to increased lacrimation. If the tonicity of the formulation is lower than 260 mOsm/kg or higher than 480 mOsm/kg, the composition becomes irritant, induces reflex tearing and blinking, and is therefore likely to reduce the bioavailability of topically instilled drugs.

In order to comply with the above physiological aspect, it has been surprisingly found that the novel ophthalmic solutions of the instant invention show an osmolarity between 300 and 400 mOsm/Kg. Small adjustments, if necessary, can be achieved with small amounts of NaCl or of trehalose.

A preferred embodiment on the instant invention is that the pharmaceutical compositions, in the form of a sterile preservative-free aqueous solution for ophthalmic use, can optionally contain HPMC (hydroxypropylmethylcellulose) or alternatively CMC (carboxymethylcellulose) or sodium hyaluronate or hyaluronic acid, in order to obtain an optically clear fluid of high viscosity, mimicking the characteristics of the human aqueous fluid. More specifically HPMC, CMC, sodium hyaluronate or hyaluronic acid have demonstrated to prolong the precorneal contact time, and subsequently improve ocular bioavailability of the drug. According to another preferred embodiment of the invention, HPMC, CMC, sodium hyaluronate or hyaluronic acid in the preparation of the instant pharmaceutical compositions can be optionally used at a concentration varying from 0.1% to 0.5%, more preferably between 0.1% to 0.3% by weight with respect to the total volume of the solution.

In another preferred embodiment, in alternative to the monodose strip, the sterile preservative-free ophthalmic solution of the invention is dispensed by using the innovative delivery system Iridya® (Silgan Dispensing Systems), a breakthrough multidose eye dropper to apply preservative-free formulations with high volumetric precision.

Alternatively the lyophilized powder mixture of melatonin tripartate adduct and trehalose can be advantageously mixed to other suitable pharmaceutical excipients in order to yield a sterile ophthalmic ointment manufactured according to the procedures well known to a person skilled in the art. Suitable excipients for the classic preparation of an ointment are liquid paraffin in a concentration range between 5% and 25%, more preferably between 10% and 20%, optimally 15%, anhydrous lanolin between 1% and 15%, more preferably between 5% and 10%, optimally 10% and white vaseline between 60% and 95%, more preferably between 70% and 85%, optimally 73.5%.

Overall, ophthalmic ointments offer the advantages to reduce dilution of the medication via the tear film, resistance to nasolacrimal drainage, and an increased precorneal contact time, despite can cause temporaneous blurred vision and matting of the eyelids with mild discomfort. Ointments are therefore generally used in combination with eye drops, which can be administered during the day, while the ointment is preferably applied at night time, when clear vision is not required.

The invention further relates to the use of melatonin tripartate for the preparation of a medicinal composition at variable concentrations suitable to elicit the desired pharmacological and therapeutic effects to prevent or treat the eye diseases for which said preparation has been designed thereof or intended to.

Therefore, the amount of melatonin tripartate, expressed as melatonin, to be administered to each eye can vary from 10 µg to 200 µg more particularly between 20 µg and 50 µg. A more preferred embodiment of the instant invention is that applicant has surprisingly found that the more suitable dose is in the range of 25 µg each eye.

The pharmaceutical product of the present invention may be further administered to the eye in a variable amount of from 1 to 8 drops per day. Each drop can further deliver a variable volume comprised between 20 µl and 50 µl or as differently required. Equivalent doses of melatonin may be further administered as other pharmaceutical compositions already disclosed within the frame of the current invention, more specifically as ointment. Moreover, similar concentrations of melatonin tripartate of the invention are further advantageously adopted to prepare the ophthalmic viscosurgical devices (OVDs) where the tripartate adduct is admixed with higher concentrations either of HPMC (hydroxypropylmethylcellulose) or CMC (carboxymethylcellulose) or sodium hyaluronate or hyaluronic acid.

It has been further advantageously evidenced that, when administered to animal (mouse or rabbit) models, melatonin tripartate eye drop solution at the used concentrations has not evidenced signs of ocular adverse reaction, inflammation or tissue damage (confidential data not shown), thus confirming to be safe with a good tolerance of single and repeated doses.

The pharmaceutical composition of the instant invention is explained in more details with reference to the following examples, which are provided by way of illustration only and should not be construed as limit to the scope of the claims in any manner.

EXAMPLE 1

Production of Melatonin Tripartate Adduct and Trehalose

Melatonin (0.1 mole; 23.2 g), adenosine (0.4 moles; 106.8 g) and glycine (0.1 mole; 7.54 g), at a molar ratio 1:4:1 respectively, were dissolved in about 1 litre of a solvent mixture (water/ethanol 70%-30%), To each sample was added trehalose (1.5%) by weight as cryoprotectant agent. The solution was filtered and lyophilized to yield melatonin tripartate adduct with 1.5% trehalose (about 152.54 g, molecule melatonin 23.28 g=15.26%). The lyophilized powder was accurately recovered and dissolved in ethanol at about a concentration of 5 mg/ml. During the precipitation process the flow rate of melatonin solution was adjusted to 2 ml/min and the flow rate of water was adjusted to 10 ml/min. A gas pressure of 0.2 bar was used to ensure the production of homogenous lyophilized powder. Microjet reactor temperature was adjusted to 25-40° C. throughout the precipitation process. The lyophilized samples contained added trehalose (1.5%) by weight as cryoprotectant agent. The obtained sterile lyophilized powders were dispersed in sterile water to obtain a concentration of melatonin tripartate adduct+trehalose of about 6 mg/ml for all preparations. The concentrations of the obtained mixtures of melatonin tripartate adduct and of trehalose have been reported here below in Table 1.

TABLE 1

| Sample mixture n. | Melatonin tripartate + Trehalose concentration mg/ml | Melatonin concentration mg/ml | Trehalose concentration mg/ml and (%) |
|---|---|---|---|
| 1 | 2.69 | 0.41 | 1.5 (0.15%) |
| 2 | 2.75 | 0.42 | 1.5 (0.15%) |
| 3 | 2.62 | 0.40 | 1.5 (0.15%) |

All formulations proved to be soluble and to yield a transparent solution of the desired nominal concentration of melatonin tripartate.

EXAMPLE 2

Production of Sterile Melatonin Tripartate Ophthalmic Solution and Package in Preservative-Free Multidose Containers [0.4 mg MLT/ml=20 µg MLT/50 µl=drop¹⁄₂₀ ml=2.62 mg/ml MLT-TRP]

The sterile lyophilized powder (13.35 g) resulting from sample mixture 1 of Example 1 have been further dissolved in sterile bidistilled water to yield 5.0 litres solution, then sterilized by filtration in aseptic conditions using 0.22 µm sterilizing membrane filter. An aliquot of about 2.0 litres of the collected sterile solution is then apportioned into sterile containers (multidose strips of eye drops each of 0.5 ml volume resulting 3570 strips) and 2.5 litres remnant volume is used to fill in aseptic conditions 460 special preservative-free S ml multidose container equipped with a volumetric precision drop dispenser. All batches tested for pH (result=7.4), melatonin potency (result=99.1% of declared nominal dose), clarity (result=limpid & transparent), osmolarity (result=335 mOsm/kg), sterility (result=conform) and eye tolerance test (results=complies with the test).

EXAMPLE 3

Production of Melatonin Tripartate Sterile Ophthalmic Ointment [1.5 mg MLT/g=3.93 mg/g MLT-TRP]

Sterile lyophilized powder of melatonin tripartate adduct (7.86 g) resulting from sample mixture 1 of Example 1, has been thoroughly admixed in aseptic conditions with a suitable mixer with 2000 g of a sterile mixture of pharmaceutical grade excipients consisting of liquid paraffin 15%, anhydrous lanolin 10% and white vaseline 73.5% to yield 1830 g of a pale whitish semisolid ointment. The bulk ointment has bee then apportioned aseptically in 3 grams tubes of melatonin tripartate each, resulting 520 tubes of sterile ophthalmic ointment with a production yield of 85%.

The batch was tested for melatonin potency (result=98.7% of declared nominal value), pH (result=7.2) and sterility (result=conform).

EXAMPLE 4

Treatment of Uveitis with Ophthalmic Melatonin Tripartate Sterile Solution

Experiment was conducted in 12 male chinchilla rabbits weighing 2 kg each. In 8 rabbits, acute immunogenic uveitis was induced in both eyes. Melatonin tripartate adduct eye drop solution and trehalose of Example 2, at the active concentration of melatonin 0.5 mg/ml, and the placebo solution consisting of 0.9% saline solution and 3% of trehalose, both packed in the special preservative-free multidose container equipped with a 25 µl drop-volume special dispensing system, have been used for test Two groups of 4 animals received the drop instillation according to the scheme reported hereby: the first group received 25 µl of melatonin (as tripartate adduct) eye drops solution; the second group received placebo solution in the same ratio. The solutions were dropped 3 times daily into both eyes for 8 consecutive days.

| Rabbit Group n. | Rabbit n. | Treatment |
|---|---|---|
| 1-Healthy (control) | 4 | no treatment |
| 2-Placebo | 4 | saline solution (25 µl, 3 times/day for 8 consecutive days) |
| 3-Melatonin tripartate | 4 | melatonin tripartate eye drops solution (25 µl melatonin, 3 times/day for 8 consecutive days) |

In animals treated with melatonin tripartate eye drops solution, a significant reduction of conjunctival oedema, corneal oedema, and iridial oedema has been recorded.

All animals with uveitis exhibited reduction of antioxidant activity (AOA) of tears, increasing of SOD (superoxide dismutase) and $\alpha_2$-macroglobulin demonstrating pronounced oxidative stress. Table 1 reports the biochemical parameters determined into the rabbit aqueous humour on day 10 of uveitis after treatment with melatonin tripartate eye drops solution and placebo.

TABLE 1

| Group | Antioxidant Activity (µM) | SOD (mg/ml) | $\alpha_2$-Macroglobulin (nmol/min · ml) |
|---|---|---|---|
| 1 | 856.05 ± 54.16 | 0.79 ± 0.06 | 3.41 ± 1.65 |
| 2 | 342.01 ± 59.98* | 22.1 ± 0.91* | 18.64 ± 2.63* |
| 3 | 504.91 ± 17.01* ** | 11.31 ± 0.72* ** | 8.2 ± 1.42* ** |

*p < 0.01 compared to healthy animals
**p < 0.01 compared to animals that did not receive treatment The results showed that melatonin tripartate eye drops solution when administered in eye drops to rabbits affected by uveitis showed a remarkable anti-inflammatory effect due to the antioxidant activity of melatonin.

EXAMPLE 5

Protective Effect of Melatonin Tripartate in a Rat Pups Model of Induced Cataract 60 Sprague-Dawley albino rat pups having an average weight of 10 g±1 g, were randomized into 3 groups:
  Group A received subcutaneous injection of normal saline.
  Group B injected with 40 µmole sodium selenite/kg subcutaneously and treated with one drop of 0.9% sodium chloride ophthalmic solution twice daily during 30 consecutive days and considered as positive control.
  Group C injected with 60 µmole/kg sodium selenite subcutaneously and treated at the same time with one drop of 10 µg melatonin (as tripartate) ophthalmic solution, instilled twice daily during 30 consecutive days.

The obtained results, reported in the Table 2 hereby, indicate that the treatment of rats with eye drops solution of melatonin (as tripartate) 10 µg eye drop twice daily, starting on the day of sodium selenite injection during 39 days, decreased the cataract formation after 15 and 21 days of treatment;

TABLE 2

| | Incidence of cataract % | |
|---|---|---|
| Group | 15 days | 21 days |
| A | 0 | 0 |
| B | 27 | 53 |
| C | 32.53 | 14.78 |

EXAMPLE 6

Protection with Melatonin Tripartate from Oxygen-Induced Retinopathy (OIR) in Pups Mice Model Pups mice model were exposed to 75% oxygen for 5 days and then returned to room air (21% oxygen). The mice were randomly divided into 3 groups:
  Control group: kept in room air (21% oxygen);
  OIR (oxygen-induced retinopathy) group: exposing to 75% oxygen (without treatment);
  OIR (oxygen-induced retinopathy)+melatonin tripartate group: exposing to 75% oxygen+10 µg melatonin (as tripartate) eye drops solution one in each eye twice day during the period of exposure to 75% oxygen.

The effects of melatonin on the expression of inflammatory factors in the retina of OIR mice have been investigated and tabulated hereby. The results of Table 3 show significant overexpression of the protein levels of TNF-α and IL-1β in retinas of OIR mice, which were downregulated following to melatonin adduct treatment

TABLE 3

| Group | TNF-α (%) | IL-1β (%) |
|---|---|---|
| Control | 0 | 0 |
| OIR (non treated) | 43.6 | 59.8 |
| OIR + Mel Trip | 21.7 | 18.43 |

OIR = mice with oxygen-induced retinopathy
Mel Trip = melatonin tripartate

Reported results of the above Table show that melatonin tripartate significantly reduced inflammatory cytokines expression in the retina of OIR model.

EXAMPLE 7

Melatonin Tripartate Effects on the Intraocular Pressure (IOP) in Glaucomatous Mice The study was carried out on 15 normal adult mice (Group A-control) and 15 glaucomatous mice (Group B). Mice were housed in temperature- and light-controlled rooms maintained according to a 12-hour light/dark cycle; all animals were fed ad libitum and studied at age 3, 6, 9, and 12 months.

Melatonin tripartate eye drops solution was administered to the cornea at a concentration of 25 μg of melatonin (as tripartate) in both eyes. Control group received the same volume of 0.9% saline solution. The intraocular pressure (IOP) was measured each hour for 5 hours being the main risk factors for the development of glaucoma producing changes in the retina and optic nerve.

The obtained results have been reported in Table 4 and evidenced that melatonin tripartate decreased IOP in glaucomatous mice, respectively, with a maximum effect at 4 hours in both groups of animals.

TABLE 4

| Group | IOP (% of control) | | | | | |
|---|---|---|---|---|---|---|
| | 0 h | 1 h | 2 h | 3 h | 4 h | 5 h |
| A | 162 | 160 | 163 | 159 | 157 | 158 |
| B | 153 | 160 | 153 | 140 | 115 | 141 |

The administration of melatonin tripartate eye drops produced an acute hypotensive effect, reducing the progressive increase of IOP in a recognized model of glaucoma, protecting the retina from further progression of this pathology.

EXAMPLE 8

Protective Effect of Melatonin Tripartate in Diabetic Rat Retina

The fluorescein leakage test (FLT) provides information on the effects of xenobiotics on the impermeability (gate function) of epithelial cell monolayers, and their recovery after exposure. The study was carried out on 21 male Wistar rats (weighing 200-250 g), maintained at a 12-h light/dark cycle (lights on from 07:00 to 19:00). Food and water were provided ad libitum, and the room temperature was maintained.

Rats were randomly divided into three groups: (1) control group; (2) diabetic group (without treatment); (3) diabetic+ melatonin tripartate group.

The above last group was treated with 20 μg melatonin tripartate eye drop solution for each eye twice a day, 1 week after induction of diabetes and continued for 7 consecutive weeks. At the end of the experiment (8 weeks), the retinas were examined by fluorescein angiography to evidence blood vessel abnormalities in retina, after administration of 10% fluorescein sodium by intraperitoneal injection of 0.1 ml. Leakage (blood vessel abnormalities) was characterized by the presence of a hyperfluorescent lesion graded as follows: 0, no leakage; 1, slight leakage; 2, moderate leakage; and 3, prominent leakage. 8 weeks after induction of diabetes, the experiment results were tabulated and revealed the development of retinal alterations in diabetic rats. More specifically, the leakages in the diabetic group were significantly higher than in the control group, while treatment with melatonin tripartate eye drops solution during 7 consecutive weeks significantly decreased this score compared to the diabetic control group, as reported here below in Table 5.

TABLE 5

| Group | Fluorescein leakage (FLT) score |
|---|---|
| Control | 0.3 |
| Diabetic (non treated) | 2.7 |
| Diabetic + Mel Trip | 1.2 |

Met Trip = melatonin tripartate

The results are justified in view that melatonin tripartate is a direct and powerful free-radical scavenger, directly neutralizing ROS and NO as well as other toxic reactants. Melatonin tripartate eye drop solution might be beneficial in preventing retinopathy also in diabetic patients.

EXAMPLE 9

Melatonin Tripartate in the Prevention and Treatment of Various Retinal Diseases Associated with Increase of VEGF, Vascular Leakage and Angiogenesis.

The experimental study was carried out evaluating the effects produced by melatonin (as tripartate) and hypoxia-inducible factor-1α(HIF-1α) protein levels in retinal pigment of epithelial cells under hypoxia.

Retinal pigment epithelial cells ($2 \times 10^6$ cells/well) were cultured with $CoCl_2$ (cobalt chloride) at 150 μM with or without melatonin (as tripartate) ($10^{-5}$ to $10^{-11}$ M) for 24 h. Protein was extracted from cultured cells. HIF-1α, ELISA kit was used for the measurement of intracellular HIF-1α, protein, and the results were expressed as percentages of the control (cells cultured under normoxia and without melatonin tripartate adduct) (mean±SD, n=3). HIF-1α, protein level in the controls was 89.1 pg/mg protein. The results are reported in following Table 6:

TABLE 6

| Group | VEGF (% Control) |
|---|---|
| Normoxia | 100 |
| $CoCl_2$ (150 μM) | 260 |
| Melatonin (as tripartate) ($10^{-11}$M) | 255 |
| Melatonin (as tripartate) ($10^{-8}$M) | 230 |
| Melatonin (as tripartate) ($10^{-8}$M) | 70 |

*P < 0.05, compared with the cells cultured under hypoxia and without melatonin.

Melatonin tripartate adduct significantly inhibited hypoxia-induced accumulation of HIF-1α, protein suggesting that it may have potential value in the prevention and treatment of various retinal diseases associated with increase of VEGF, vascular leakage and angiogenesis.

EXAMPLE 10

Melatonin Tripartate for the Relief of Symptoms from Ophthalmic Conjunctivitis by SAR-CoV-2

On days 8 and 9 of hospitalization (disease day 12 and 13), patients reported redness, foreign body sensation, and tearing in both eyes, without blurred vision. They excluded that they had touched their eyes with their hands. Slit-lamp examination bilaterally showed moderate infection of the conjunctiva, conjunctival follicles of the lower eyelid and preauricular and palpable lymph nodes. No sub-conjunctival haemorrhage or corneal lesions or anterior chamber inflammation were observed. Slit lamp scans showed clear signs of acute viral conjunctivitis. The examination of the disease on days 12 and 13 showed a moderate conjunctival infection and follicles of the conjunctiva of the lower eyelid. Clinical examinations on day 17 of the disease and on day 19 showed that treatment with the adduct of melatonin ophthalmic drops (20 µg of melatonin/drop of solution three times a day for 12 days) in each eye gradually attenuated the onset of symptoms. The clinical presentation of the cases met the criteria for acute viral conjunctivitis. It is likely that the ophthalmic drops of the melatonin adduct of the invention have significantly contributed to the treatment of symptoms. Conjunctival swabs tested positive for SARS-CoV-2 RNA for at least 5 days before Ct values gradually decreased. Conjunctival swab values remained positive (Cycle Cutoff: 38.47) but showed a trend of decreasing values and signs of clinical improvement. The conjunctival swabs remained positive for SARS-CoV-2 until days 14 and 17 after the onset of the disease. On day 19 RT-PRC tested negative for SARS-CoV-2. Conjunctival specimens were negative for SARS-CoV-2 on day 19 and day 20 of illness, respectively. In conclusion SARS-CoV-2 is capable of causing ophthalmic complications such as viral conjunctivitis in the intermediate phase of the disease. The aim of this study is to report the ocular characteristics and the presence of viral RNA of acute respiratory syndrome of coronavirus 2 (SARS-CoV-2) in conjunctival swabs of two patients suffering from confirmed new coronavirus disease 2019 (COVID-19). Written informed consent was obtained from the respective patients. Participants aged 38 and 62 with confirmed COVID-19 and bilateral acute conjunctivitis appeared 12 and 13 days after the onset of the disease. Based on the detailed ophthalmological examination, reverse transcription PRC (RT-PRC) was performed to confirm the presence of the SARS-CoV-2 virus. Acute viral conjunctivitis improved clinically significantly following administration of 20 µg melatonin/drop of solution three times a day for 12 consecutive days. However, conjunctival sampling may not be useful for early diagnosis as the virus may not initially be present in the conjunctiva.

Therefore, the present invention is well adapted to carry out the objects and attain the ends and advantages mentioned as well as those that are inherent therein. While numerous changes may be made by those skilled in the art, such changes are encompassed within the spirit of this invention as defined by the appended claims.

The invention claimed is:

1. A soluble pharmaceutical composition comprising (i) a melatonin tripartate adduct (MTA) of general formula (I):

and, (ii) trehalose in an amount of from 1% to 5% by weight, wherein MTA is adducted to the nucleoside adenosine in the presence of $C_2$-$C_5$ low-chain amino acid, wherein a melatonin moiety, adenosine and glycine have a molar ratio range varying from 1:1:1 up to 1:6:1, wherein the MTA is in a form of a stable sterile lyophilized powder.

2. The pharmaceutical composition according to claim 1, wherein the melatonin is of pharmaceutical grade with a purity content of at least 99.0%, calculated on a dry basis.

3. The pharmaceutical composition according to claim 1, wherein the melatonin moiety, adenosine and glycine have a molar ratio of 1:4:1.

4. The pharmaceutical composition according to claim 3, wherein the melatonin tripartate adduct (MTA) has a solubility in water at least 300 fold greater compared to melatonin alone.

5. The pharmaceutical composition according to claim 1, wherein a concentration of the melatonin tripartate adduct (MTA) varies from 0.01 mg/ml to 10 mg/ml in sterile distilled water or physiological saline solution.

6. The pharmaceutical composition according to claim 1, wherein pharmaceutical grade trehalose is admixed to the melatonin tripartate adduct (MTA) at an amount so that the final concentration of the trehalose in the composition is from about 1.5% to 3% by weight.

7. The pharmaceutical composition according to claim 1, wherein the sterile lyophilized powder of the MTA is admixed to trehalose and is dissolved in sterile water in aseptic conditions to yield a sterile ophthalmic solution of melatonin tripartate to elicit a desired therapeutic effects of the adduct when intended and/or addressed to the ophthalmic field.

8. The pharmaceutical composition according to claim 7, further optionally containing at least one of: retinol, sodium hyaluronidate, hyaluronic acid, L-carnosine, L-acetylcarnosine or mixtures thereof.

9. The pharmaceutical composition according to claim 7, further optionally containing at least one of: hydroxypropylmethylcellulose (HPMC), carboxymethylcellulose (CMC), sodium hyaluronate, or hyaluronic acid, to yield an ophthalmic viscosurgical device (OVD) with a viscosity suitable for ophthalmic surgery.

10. The pharmaceutical composition according to claim 9, wherein HPMC or CMC is in a range from 0.1% to 0.5%, or sodium hyaluronate or hyaluronic acid is 1% by weight with respect to the total weight of the solution.

11. The pharmaceutical composition according to claim 7, wherein the pharmaceutical composition is in the form of a sterile gel, emulsion or ointment, where the latter comprises a pharmacologically effective amount of melatonin tripartate and suitable excipients for the conventional preparation of an ointment including liquid paraffin at a concentration between 5% and 25% by weight, anhydrous lanolin between 1% and 15% by weight, and white petroleum jelly between 60% and 95% by weight.

12. The pharmaceutical composition according to claim 7, having a pH in a range between 7.0 and 7.7.

13. The pharmaceutical composition according to claim 7, having an isotonicity of the solution in a range from 260 to 480 mOsm/kg.

14. The pharmaceutical composition according to claim 7 for the treatment of oculopathies and ophthalmic diseases of the posterior segment of the eye by intraocular or topical ocular administration, wherein the melatonin tripartate adduct (MTA) has a concentration varying from 0.01 mg/ml to 10 mg/ml, where the pharmaceutical composition is sterile and preservative-free.

15. A process for preparing a sterile preservative-free ophthalmic solution of melatonin tripartate adduct, comprising the steps of:
  (i) preparing melatonin tripartate adduct (MTA) sterile lyophilized powder of claim 1 by adducting a melatonin moiety, adenosine and glycine at the molar ratio of 1:4:1, by a conventional lyophilisation process;
  (ii) admixing in sterile environment said sterile lyophilized powder consisting of melatonin tripartate adduct in a volume of distilled water and then with an amount of pharmaceutical grade trehalose;
  (iii) adding any one of retinol, sodium hyaluronidate, hyaluronic acid, L-carnosine, or L-acetylcarnosine or a mixture thereof, and admixing thoroughly to yield a clear and transparent solution;
  (iv) adjusting the pH to about 7.4 and the osmolarity within the parameters of 310 and 350 mOsm/kg;
  (v) processing the solution from step (iv) through a sterilizing membrane or cartridge filter to meet predetermined sterility requirements; and
  (vi) apportioning a fixed volume of the preservative-free sterile ophthalmic solution from step (v) into a primary unit-dose strip or multi-dose container equipped from a drop-metering system, using nitrogen as a purge and process gas.

16. A packaged unit-dose or multi-dose container, holding from 0.2 to 20 ml of the sterile preservative-free ophthalmic solution of melatonin tripartate adduct (MTA) produced by the method of claim 15 for ophthalmic indications.

17. The packaged unit-dose or multi-dose container according to claim 16, wherein the sterile preservative-free ophthalmic solution of melatonin tripartate adduct (MTA) is dispensed at between 10 g and 200 g/dose of melatonin in each eye.

18. A method of treating a human ophthalmic disease or clinical condition, said method comprising administering an effective amount of the sterile preservative-free ophthalmic solution of melatonin tripartate adduct (MTA) of claim 17 into the periocular area in a subject in need thereof.

19. The method according to claim 18, where the disease or clinical condition is selected from the group consisting of retinopathy of prematurity (ROP), cataract in babies and strabismus, degenerative ophthalmic diseases as choroidal neovascularization (CNV), retinal vein occlusion (RVE), retinitis and optic neuritis (ON), uveitis, glaucoma, retinal glaucomatous, cataract, age-related macular degeneration (AMD), retinitis pigmentosa (RP), pathological myopia (PM), photocheratitis, amblyopia, chorioretinopathy, diabetic macular degeneration (DM D), diabetic macular edema (DME), proliferative diabetic retinopathy and retinal detachment.

20. The method according to claim 18, where the disease or clinical condition is selected from the group consisting of diseases with high inflammatory expression as dry eye syndrome (DES), computer vision syndrome or display device syndrome (CVS), and ocular changes during and after space travel.

21. The method according to claim 18, where the disease or clinical condition is selected from the group consisting of ophthalmic diseases or conditions from bacterial or viral origin including trachoma, ocular toxoplasmosis, ocular malaria, virus-related posterior uveitis infections including human herpes virus, measles, rubella, and arboviruses including Ebola, Marburg, Dengue, West Nile, Chikungunya, SARS-CoV-2 and Zika.

22. The method according to claim 18, where the disease or clinical condition is selected from the group consisting of injuries and inflammation induced by peri- and post-ophthalmic surgery and oxidative stress in affected subject.

\* \* \* \* \*